United States Patent [19]

Ishikawa et al.

[11] 4,289,847
[45] Sep. 15, 1981

[54] METHOD OF FORMING DYE IMAGE

[75] Inventors: Wataru Ishikawa; Mitsuto Fujiwhara; Tamotsu Kojima; Takaya Endo; Katsunori Kato, all of Hino, Japan

[73] Assignee: Konishiroku Photo Industry Co., Ltd., Tokyo, Japan

[21] Appl. No.: 170,770

[22] Filed: Jul. 21, 1980

Related U.S. Application Data

[63] Continuation of Ser. No. 4,768, Jan. 19, 1979, abandoned.

[30] Foreign Application Priority Data

Jan. 20, 1978 [JP] Japan ............................ 53-5666

[51] Int. Cl.$^3$ .............................................. G03C 7/00
[52] U.S. Cl. .................................. 430/389; 430/557; 430/558
[58] Field of Search ......................... 430/389, 557, 558

[56] References Cited

U.S. PATENT DOCUMENTS

| | | | |
|---|---|---|---|
| 3,990,896 | 11/1976 | Arai et al. | |
| 4,095,983 | 6/1978 | Wolff et al. | |
| 4,106,942 | 8/1978 | Tanaka et al. | |
| 4,133,958 | 1/1979 | Boie et al. | 430/389 |
| 4,138,263 | 2/1979 | Boie et al. | |
| 4,221,860 | 9/1980 | Hirose et al. | 430/389 |

FOREIGN PATENT DOCUMENTS

| | | |
|---|---|---|
| 2600166 | 7/1976 | Fed. Rep. of Germany |
| 2713022 | 9/1977 | Fed. Rep. of Germany |

Primary Examiner—J. Travis Brown
Attorney, Agent, or Firm—Bierman & Bierman

[57] ABSTRACT

The present invention relates to a method of forming a dye image which involves processing a light-sensitive silver halide photographic image, after its imagewise exposure, in the presence of a novel yellow coupler as depicted in the formula below and an aromatic primary amine color developing agent

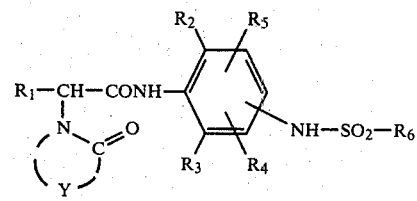

wherein $R_1$ represents cyano, alkyl carbonyl, phenylalkyl carbonyl, phenoxy alkyl carbonyl, phenylthio alkyl carbonyl, arylcarbonyl, alkyl phenyl carbonyl, alkoxy phenyl carbonyl, $R_2$, $R_3$, $R_4$, $R_5$ independently are hydrogen, halogen, alkyl, alkoxy, aryloxy, alkylacyloxy, arylacyloxy, acylamino, N-alkyl carbamoyl, N-phenylcarbamoyl, alkylsulfonamido, arylsulfonamido, N-alkyl sulfamoyl, N-phenylsulfamoyl, or imido, $R_6$ represents cycloalkyl, alkenyl, naphthyl, thienyl, benzothienyl, furyl, or pyranyl, or a group of the formula (II):

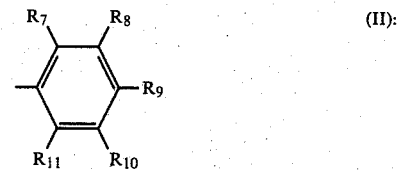

wherein $R_7$, $R_9$ and $R_{11}$ are each hydrogen or alkyl, the sum of the carbon atoms in $R_7$, $R_9$ and $R_{11}$ being 5 to 20, $R_8$ and $R_{10}$ are hydrogen, and Y represents non-metal atoms required for forming 2,5-dioxo-imidazolidine, 2-3,5-trioxo-imidazolidine, 2,5-dioxo-triazolidine, 2,4-oxazolidinedione, 2,4-thiazolidinedione, 2(1H)-pyridone, 2(1H)-pyrazone, 5(1H)-imidazolone, 5(1H)-triazolone, 2(1H)-pyrimidone, 2-pyrazolone (5), 2-isothiazolone(5), 2(1H)-quinaoxazolone, 4(3H)-pyrimidone, 2-benzoxazolone, 4-isooxazolone(5), 3-fluorone(2), 4-imidazolone(2), 3-pyrazolone, 2-tetrazolone(5), 3-tetrazolone(5), and derivatives thereof.

9 Claims, 1 Drawing Figure

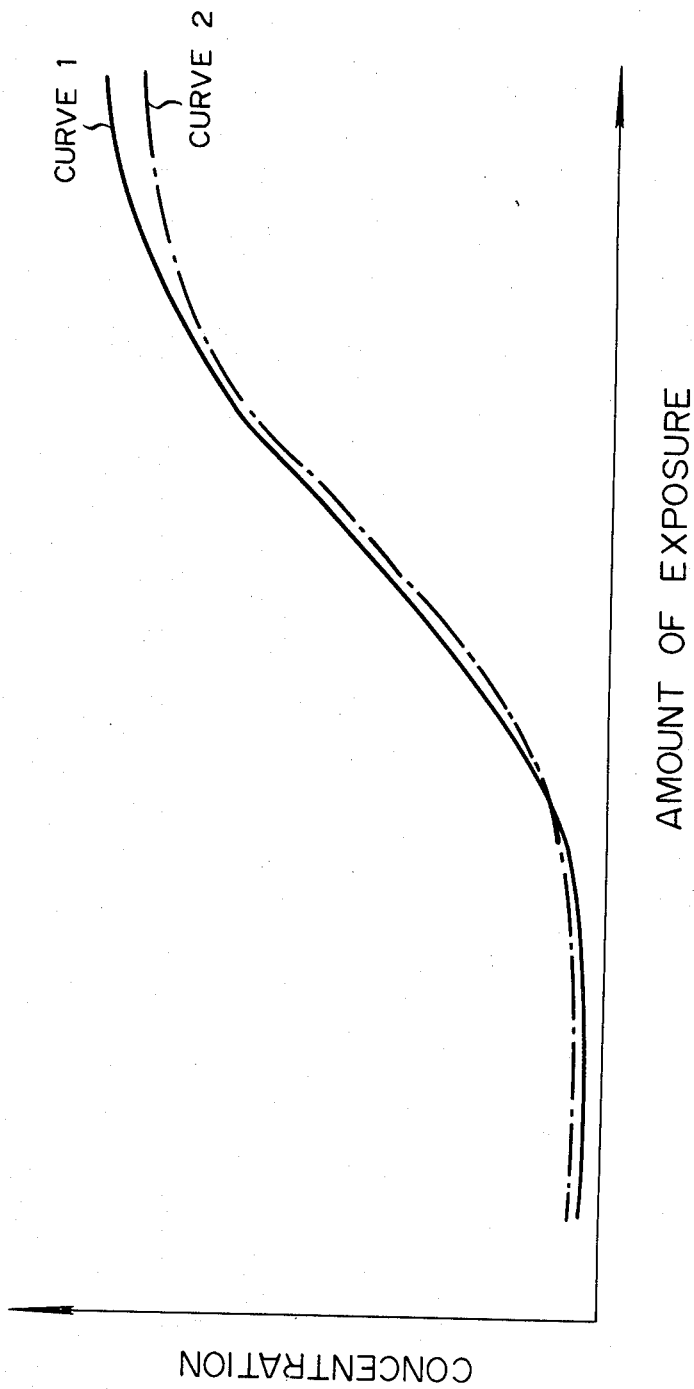

METHOD OF FORMING DYE IMAGE

This application is a continuation of U.S. Application Ser. No. 4,768 filed Jan. 19, 1979, now abandoned.

This invention relates to a method of forming a yellow dye image for use in color photography.

In color photography, it has been well known, for example, to form a dye image by color-developing a light-sensitive photographic material containing a coupler, after being subjected to exposure, with a color developing liquid which comprises as a principal ingredient an aromatic primary amino color developing agent. Among such couplers as used in this art, a yellow coupler contains an active methylene group which serves to form a yellow dye by means of coupling reaction with an oxidation product of the aromatic primary amino developing agent. When the active methylene is unsubstituted, that is in the case of yellow coupler of active point-unsubstituted type, 4 molecules of a silver halide are required for forming 1 molecule of dye in the color development. This is the reason for which the above coupler is called 4-equivalent type yellow coupler.

On the other hand, it has also been known that there is formed the yellow dye, alike in the case of a coupler of active point-unsubstituted type, also from such yellow coupler as so-called yellow coupler of active point-substituted type, in which one of the hydrogen atoms of the active methylene group is substituted by such substituent as a halogen atom, —OR group (where R represents an alkyl, aryl, heterocyclic or acyl group), —SR′ group (where R′ represents an alkyl, aryl or heterocyclic group), azo group or group of the formula

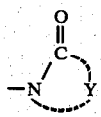

(where Y represents non-metal atoms necessary to complete a 5- or 6-membered ring). In this case, such substituents as halogen atom are split off during the course of the color developing reaction, forming 1 molecule of dye from 2 molecules of the developed silver halide. Due to this, the yellow coupler of active point-substituted type is called 2-equivalent type yellow coupler in contrast to said 4-equivalent type yellow coupler. For the reason as mentioned above, use of the 2-equivalent type yellow coupler enables reduction of cost in comparison with the case where the 4-equivalent type yellow coupler is used, because the silver halide may be satisfactory in the half amount for achieving the same color development. Further, since the 2-equivalent type yellow coupler shows high coupling speed, it has good adaptability for a high temperature and rapid processing, especially 3-bath processing comprising development, bleaching, fixing and washing with water alone. Furthermore, it is possible to reduce the thickness of an emulsion layer and to increase resolving power, sharpness of a dye image, while, when the material comprises multiple layers, permeability of light into lower layers is improved and thus the photographic speed can be improved. Because of a variety of advantages as mentioned above, the 2-equivalent type coupler is very useful for photographic use. As a mother nucleus structure of yellow coupler, α-benzoylacetanilide type yellow coupler has heretofore been primarily used. A number of them, however, show high coupling reactivity and as the result, they had such drawbacks as increased fog or poor preservability (such as stability against light, moisture, heat, etc.). Recently, α-pivalylacetanilide type yellow couplers have become to be used. These yellow couplers show lower coupling reactivity than said α-benzoylacetanilide type yellow coupler, but preservability of a dye formed is good. Due to the above facts, the investigation concerning α-pivalylacetanilide type two equivalent coupler has been made. As the method for incorporating the above coupler into a photographic emulsion, there have been known so-called protect dispersion method using a coupler by dissolving in a high-boiling organic solvent, or a low-boiling organic solvent such as ethyl acetate or butyl acetate, in place of high-boiling organic solvent, or further so-called Fischer dispersion method where a coupler is used by being dissolved in an aqueous alkaline solution. Among these methods, the protect dispersion method which is excellent in the preservability (such as light fastness, heat resistance or resistance against wetness) of the resulting dye image, or in coupling reactivity, granularity of dye and sharpness is generally useful. However, the prior couplers do not show satisfactory coupling reactivity in a system where a benzyl alcohol free color developing solution is used. Further, the prior couplers have the drawback where the coupling reactivity varies particularly due to the changing of pH value (for example) (pH 11.5–10.0) of the color developing solution.

In order to dissolve the above problems, a variety of prior arts have been known but no satisfactory state has yet been found. For example, Japanese Patent Laid-Open-to-Public No. 50-87650 describes a yellow coupler which contains a sulfonamide bonding at the 5-position of α-pivalyl-acetanilide and in which one hydrogen atom at the active point is substituted by an aryloxy group. A part of such yellow couplers possesses characteristic features that the coupling reactivity due to pH variation of the developing solution (pH 11.5–10.0) is substantially insusceptible. On the other hand, however, they possess a problem that preservability of a dye formed after color development is less than that of a yellow coupler which contains other bonding group (for example, acylamino group) at the 5-position of α-pivalylacetanilide.

Yellow couplers described in Japanese Patent Laid-Open-to-Public No. 52-115219 are unsatisfactory with respect to pH dependency, color development and preservability.

Thus, the first object of this invention is to provide a yellow coupler possessing satisfactory coupling reactivity even in a system where a color developing solution without addition of benzyl alcohol is used and a method of forming the dye image.

The second object of this invention is to provide a yellow coupler which is insusceptible to the variation of pH (10.0–11.5) of the color developing solution and enables reduction of variation of the resulting dye image and a method of forming the dye image.

The third object of this invention is to provide a yellow coupler which does not cause color contamination such as fog and is excellent in the preservability of the resulting dye image and a method of forming the dye image.

As a result of a variety of investigations, the inventors have found that the above objects of this invention are attainable by treating a light-sensitive silver halide photographic material, after its image-wise exposure, in the presence of a novel yellow coupler of the general formula I as given below and an aromatic primary amine color developing agent:

General formula I

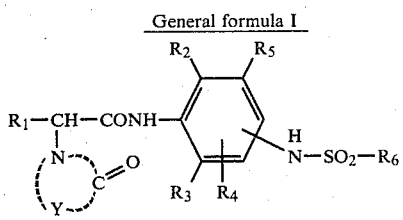

wherein $R_1$ represents a cyano group, alkyl carbonyl group which may contain a substituent (for example, methyl carbonyl group, isobutyl carbonyl group, tert.-butyl carbonyl group, n-hexyl carbonyl group, 1-methylpentyl carbonyl group, neo-pentyl carbonyl group, isohexyl carbonyl group, n-dodecyl carbonyl group, substituted alkyl carbonyl group such as phenyl-substituted alkyl carbonyl group, phenoxy-substituted alkyl carbonyl group, phenylthio-substituted alkyl carbonyl group, or the like), aryl carbonyl group which may contain a substituent (for example, phenyl carbonyl group, naphthyl carbonyl group, substituted aryl carbonyl groups such as alkyl-substituted phenyl carbonyl group, alkoxy-substituted phenyl carbonyl group or the like, the carbon atom number of said alkyl or alkoxy group being 1 to 5) but $R_1$ is not intended to be limited particularly to these groups and $R_1$ may be one of various groups known for yellow couplers of prior art; $R_2$, $R_3$, $R_4$ and $R_5$ which may be the same or different, represent independently a hydrogen atom, halogen atom (e.g. fluorine, chlorine, fluorine and iodine), group which may be substituted, such as alkyl group (e.g. methyl, methoxy-methyl, ethyl or the like), alkoxy group (e.g. methoxy, ethoxy, n-hexadecyloxy or the like), aryloxy group (e.g. phenoxy, naphthoxy, alkyl-substituted phenoxy or the like), alkyl acyloxy group (e.g. acetoxy, propionyloxy or the like), arylacyloxy group (e.g. benzoyloxy or the like), acylamino group (e.g. acetamido, γ-(2,4-di-tert.-amylphenoxy) butanamido, benzamido or the like), N-substituted carbamoyl group (e.g. methyl carbamoyl, ethyl carbamoyl, dodecyl carbamoyl, phenyl carbamoyl or the like), alkylsulfonamido group (e.g. ethanesulfonamido, hexadecanesulfonamido or the like), arylsulfonamido group (e.g. benzenesulfonamido or the like), N-substituted sulfamoyl group (e.g. N-methylsulfamoyl, N-dodecylsulfamoyl, N-phenylsulfamoyl or the like), imido group (e.g. succinimido, phthalimido or the like) and, besides the afore-mentioned groups, $R_2$, $R_3$, $R_4$ and $R_5$ may independently be further various groups and among the above groups, $R_2$ and $R_3$ are each preferably hydrogen atom, halogen atom, alkoxy group or aryloxy group and particularly preferably at least one of them is a halogen atom or alkoxy group; $R_6$ represents a group which may independently be substituted such as cycloalkyl group (e.g. cyclohexyl, cyclopentyl or the like), alkenyl group (e.g. allyl, vinyl, pentenyl, isopropenyl or the like), heterocyclic residue (e.g. thienyl, benzothienyl, furyl, pyranyl or the like), naphthyl group or group represented by the general formula II

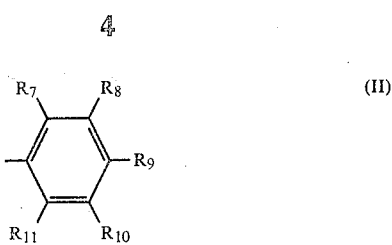

wherein $R_7$, $R_8$, $R_9$, $R_{10}$ and $R_{11}$ which may be the same or different represent independently a hydrogen atom, halogen atom (e.g. fluorine, chlorine, bromine, iodine), alkyl group which may contain a substituent (e.g. methyl, ethyl, n-propyl, n-butyl, n-pentyl, n-hexyl, n-heptyl, n-octyl, n-nonyl, n-decyl, n-dodecyl, n-tridecyl, n-tetradecyl, n-pentadecyl, n-hexadecyl, isopropyl, isobutyl, sec. butyl, tert.-butyl, isopentyl, neopentyl, tert.-pentyl, isohexylphenoxymethyl group or the like) aryl group which may be substituted (e.g. phenyl group etc.), alkoxy group which may contain a substituent, alkoxy group which may be substituted (e.g. methoxy, ethoxy, n-decyloxy, n-dodecyloxy, n-hexadecyloxybenzyloxy group or the like), aryloxy group which may be substituted (e.g. phenoxy group), substituted carbamoyl group (e.g. methyl carbamoyl, decylcarbamoyl or the like), carboxy group and its esterified form (e.g. methoxycarbonyl, ethoxycarbonyl, benzyloxycarbonyl, phenoxycarbonyl or the like), sulfo group and its esterified form (e.g. methoxysulfonyl, propyloxysulfonyl, benzyloxysulfonyl, phenoxysulfonyl or the like), substituted sulfamoyl group (e.g. N-methylsulfamoyl, N-ethylsulfamoyl, N-dodecylsulfamoyl, N-phenylsulfamoyl, N-benzylsulfamoyl), alkylsulfonamido group which may have a substituent or arylsulfonamido group which may have a substituent, with the proviso that the sum of the carbon atom number of $R_7$ to $R_{11}$ is from 5 to 20, among the above-mentioned groups the case where $R_8$ and $R_{10}$ are hydrogen atoms and $R_7$, $R_9$ and $R_{11}$ are independently hydrogen atom or the above alkl group being preferable. When a coupler in which the sum of the carbon atom number of $R_7$, $R_9$ and $R_{11}$ is 8 to 16 is applied to the incorporated type of color process, particularly excellent effect with respect to color developing properties and light-stability can be attained.

Further, also when a coupler in which $R_7$, $R_8$, $R_9$ and $R_{11}$ are independently hydrogen atoms and $R_{10}$ is a group other than the above-mentioned alkyl group having 5-20 carbon atoms is applied to the incorporated type of color process, there is attainable particularly excellent effect with respect to the color developing properties and light-stability.

Furthermore, a coupler having a group $NHSO_2R_6$ at the 5-position is used particularly preferably in the present invention.

In the general formula (I), Y represents a non-metal atom necessary to complete a 5- or 6-membered ring together with the nitrogen atom attached to the active point and the carbonyl group.

Cyclic compounds to be formed by Y are preferably represented by such substituents at the active point of yellow coupler (for example, 2,5-dioxo-imidazolidine, 2-3,5-trioxoimidazolidine, 2,5-dioxo-triazolidine, 2,4-oxazolidinedione, 2,4-thiazolidinedione, 2(1H)-pyridone, 2(2H)-pyrazone, 5(1H)-imidazolone, 5(1H)-triazolone, 2(1H)-pyrimidone, 2-pyrazolone(5), 2-isothiazolone(5), 2(1H)-quinaoxazolone, 4(3H)-pyrimidone, 2-benzoxazolone, 4-isooxazolone(5), 3-fluorone(2), 4-imidazolone (2), 3-pyrazolone, 2-tetrazolone(5), 3-tetrazolone(5), etc. and derivatives thereof) as described in Japanese Patent Publications No. 48-25933 and No. 49-13576; and Japanese Patent L-O-P Nos. 48-29432, 48-66834, 48-66835, 48-94432, 49-1229, 50-28834 and 50-158329.

As a preferable embodiment, the general formula I is rewritten in following general formula III,

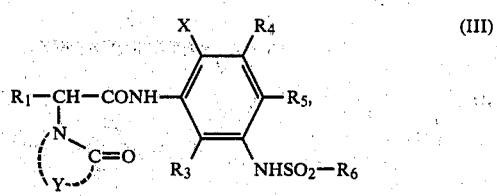

wherein X represents a halogen atom, $R_1$, $R_3$, $R_4$, $R_5$, $R_6$ and Y is same meanings as mentioned above. More preferably $R_6$ is the group represented by the general formula II. Further $R_1$ is preferably a pivalyl group.

Typical examples of couplers which can be used in this invention are shown below with any intention of limitation thereto.

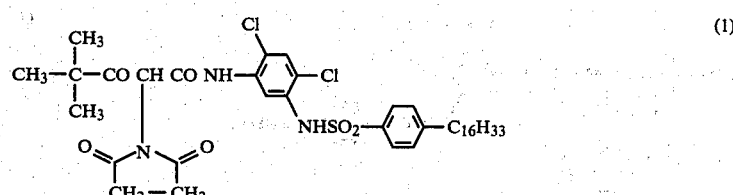

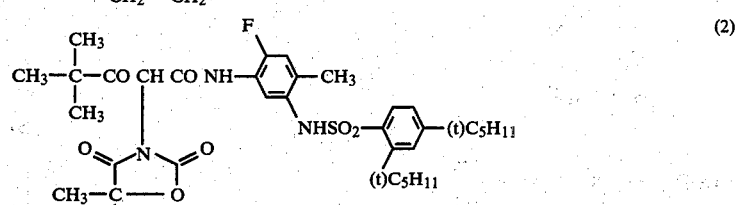

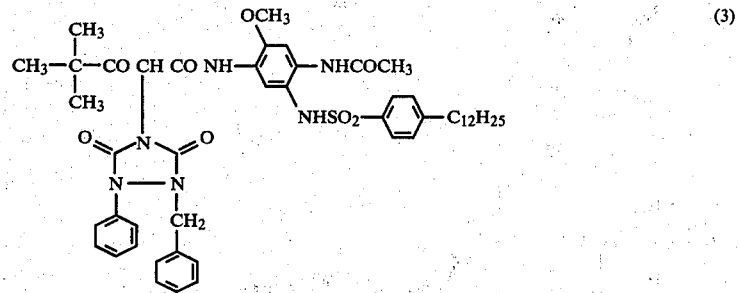

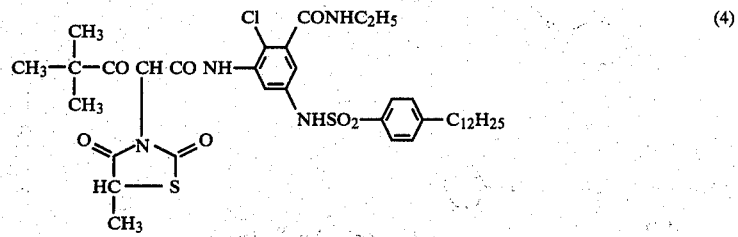

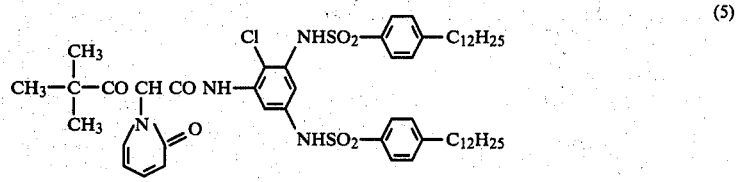

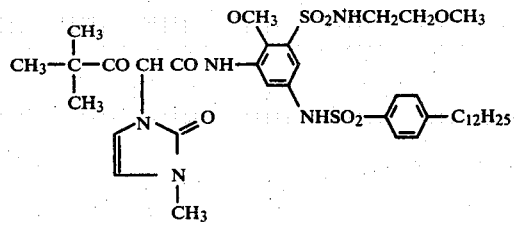
(6)
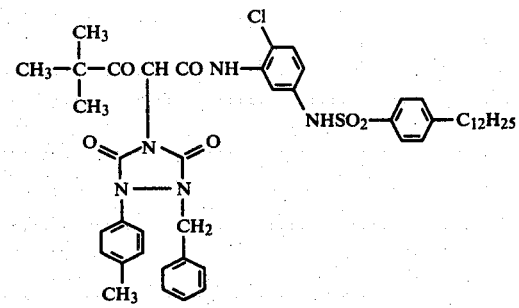
(7)
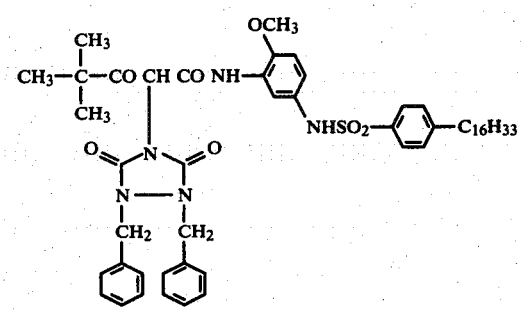
(8)
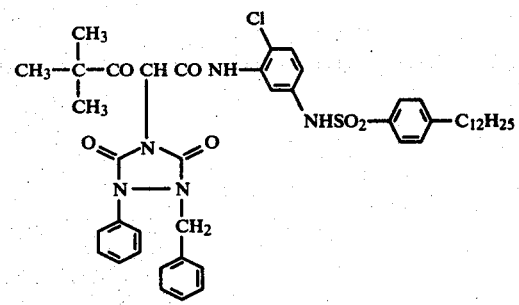
(9)
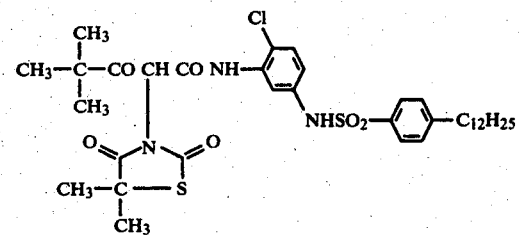
(10)
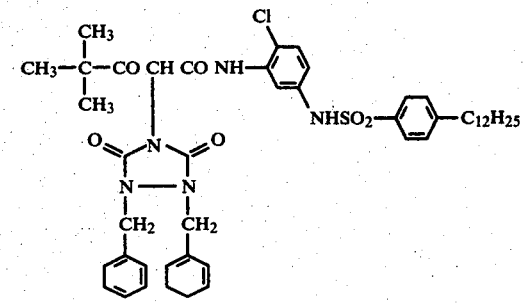
(11)

-continued
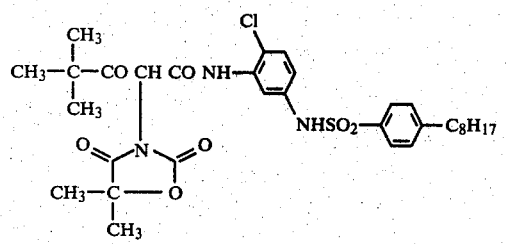
(12)
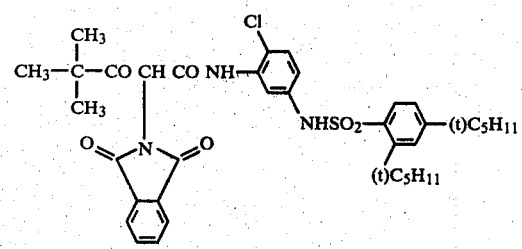
(13)
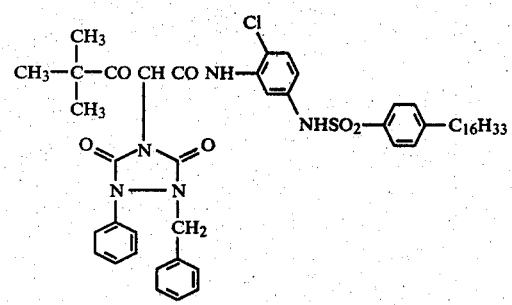
(14)
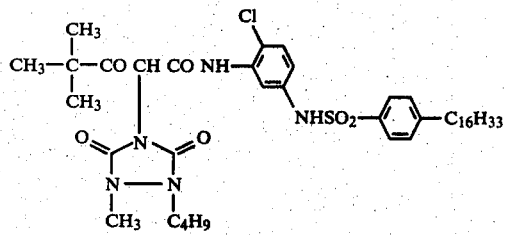
(15)
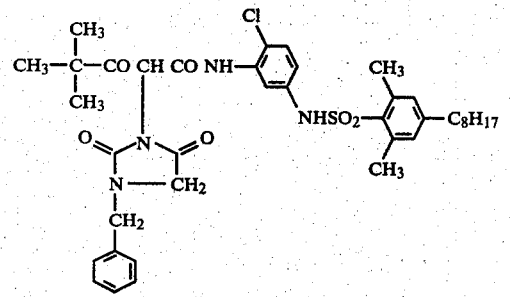
(16)
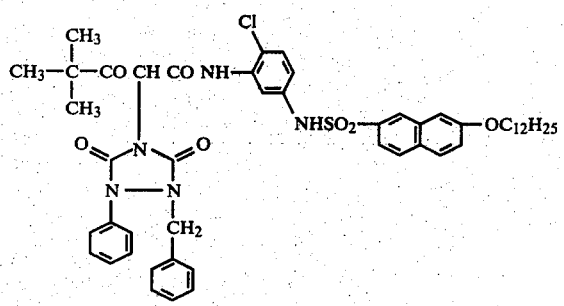
(17)

-continued
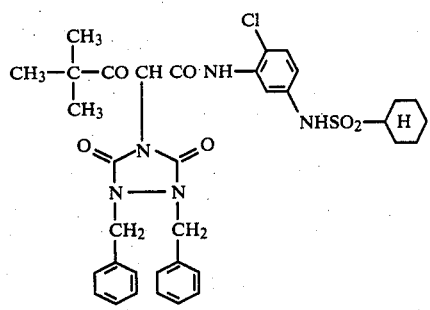 (18)
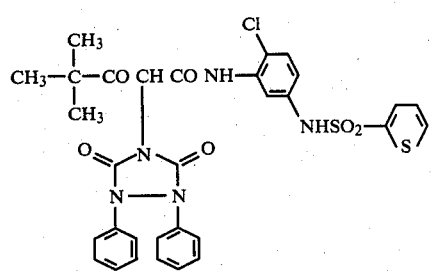 (19)
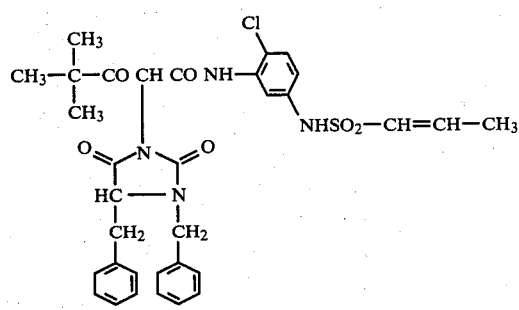 (20)
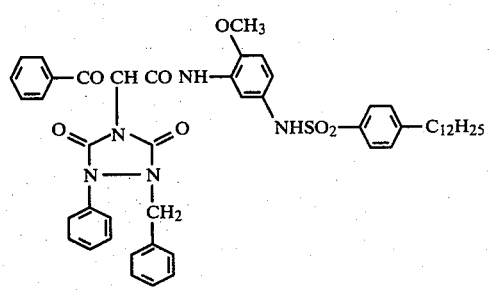 (21)
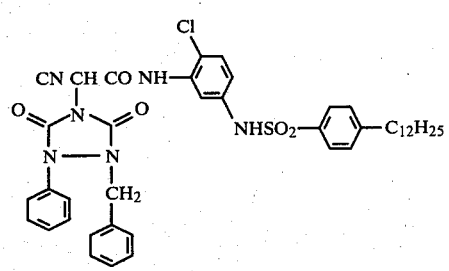 (22)

-continued
(23)
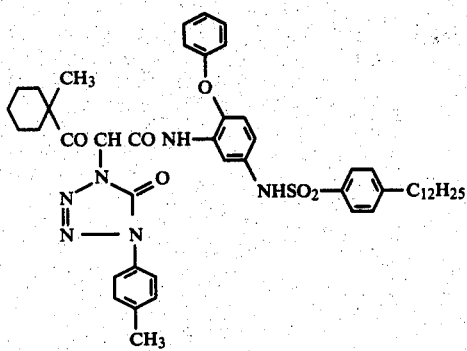
(24)
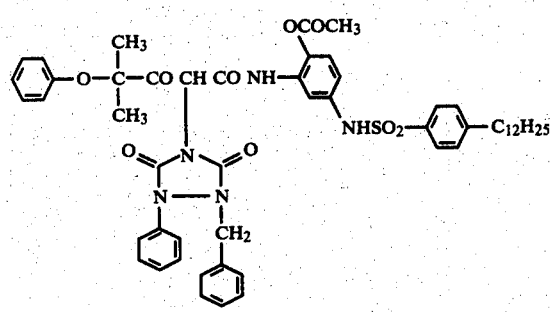
(25)
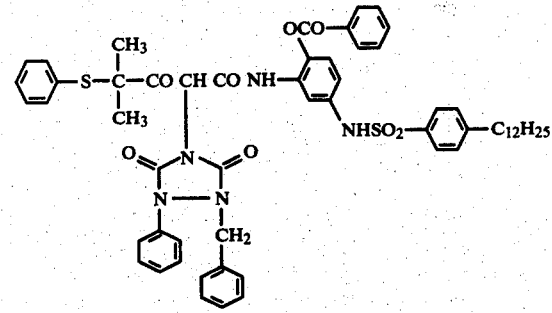
(26)
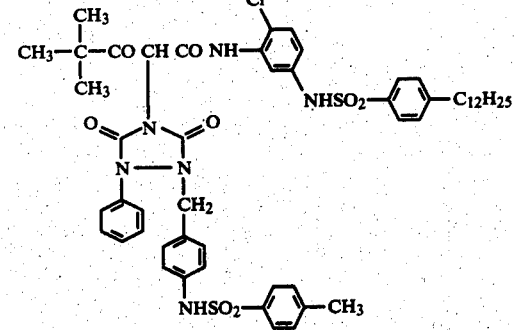
(27)
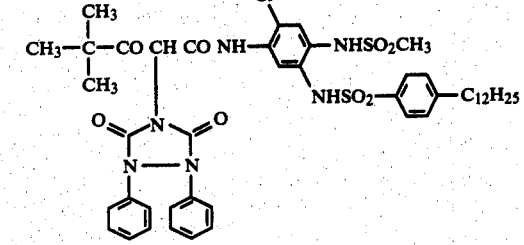

-continued
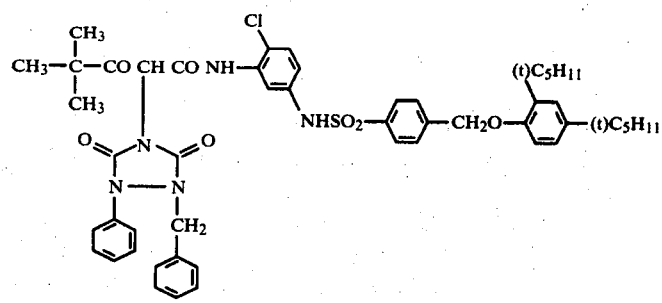 (28)
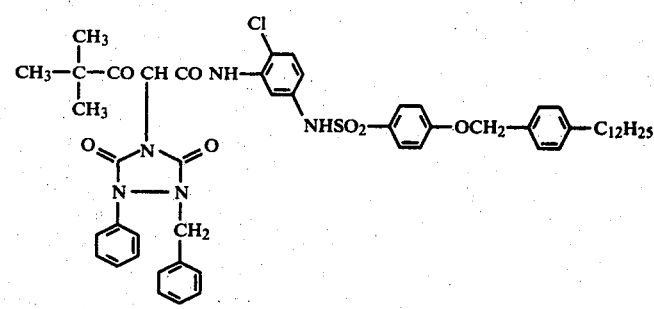 (29)
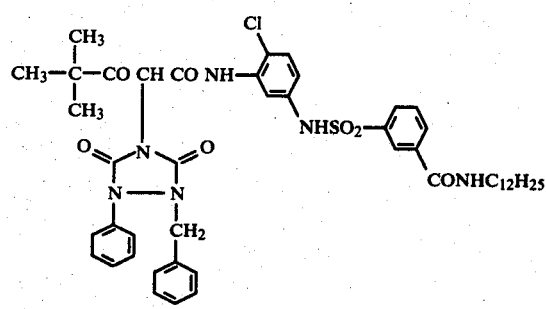 (30)
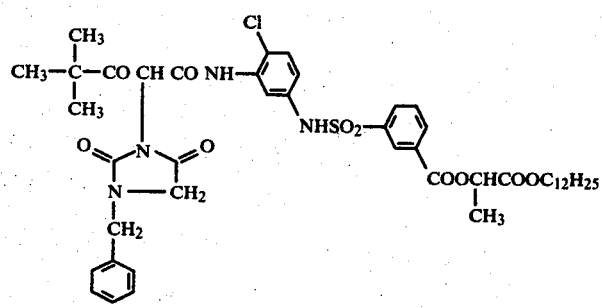 (31)
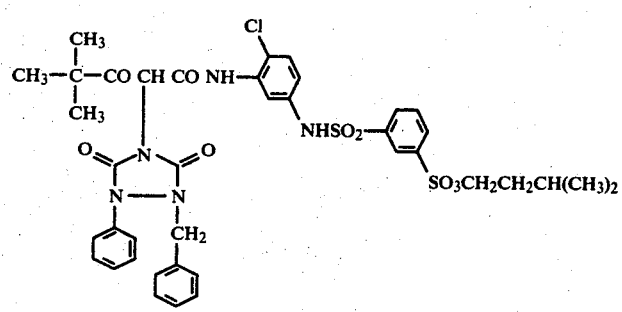 (32)

-continued
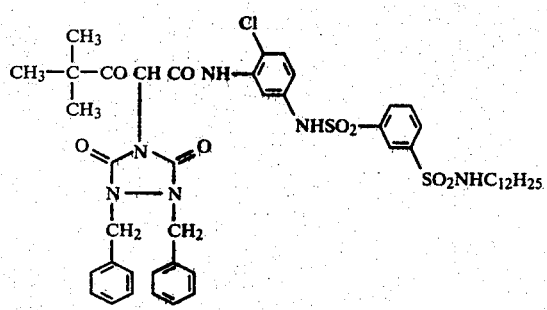 (33)
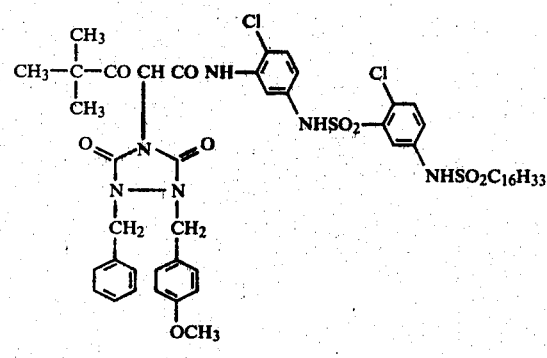 (34)
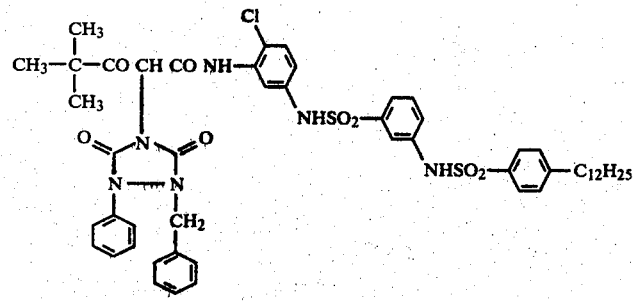 (35)
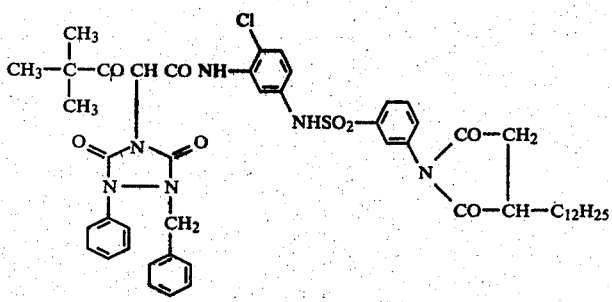 (36)
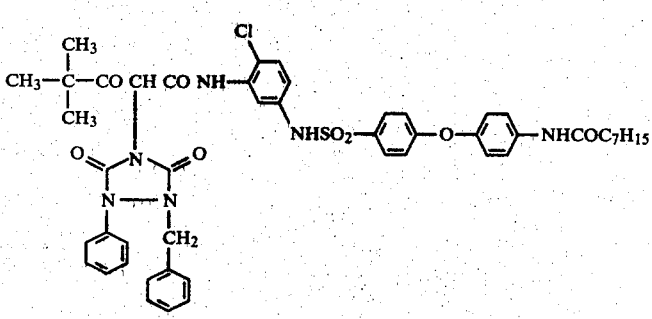 (37)

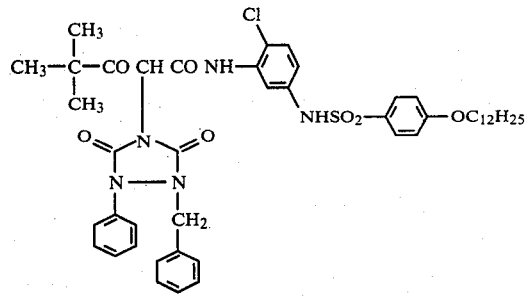

(38)

For the synthesis of the above couplers according to this invention, first, for example, 3-nitro-aniline is reacted with benzenesulfonyl chloride to form 3-nitrobenzenesulfonanilide, which is reduced to give 3-aminobenzenesulfonanilide. Then, the resulting compound is reacted with α-pivalyl-ethylacetate to form 4-equivalent yellow coupler, α-pivalyl-3-benzenesulfonamidacetanilide. Alternatively, 4-equivalent yellow coupler, α-pivalyl-3-benzenesulfonamidacetanilide can be obtained by the reaction between α-pivalyl-3-amino-acetanilide and benzenesulfonylchloride. In order to prepare 2-equivalent coupler according to this invention, the active point is halogenated and subjected to the reaction with a component to be substituted at the active point, in accordance with a prior art to give the corresponding 2-equivalent yellow coupler. Further, use of cycloalkyl-, naphthyl-, alkenyl- and heterocyclic sulfonyl chloride, respectively, in place of said benzenesulfonyl chloride produces the yellow couplers according to this invention, having the corresponding sulfonamide bonding.

Various syntheses for the exemplified compounds will be given below and it should be noted that other couplers can also be readily prepared in a similar manner.

SYNTHESIS EXAMPLE 1

(Preparation of exemplified coupler 1)

α-Pivalyl-5-amino-2,4-dichloro-acetanilide was reacted with the equimolar amount of p-hexadecylbenzenesulfonyl chloride to give α-pivalyl-2,4-dichloro-5-(p-hexadecylbenzenesulfonamide)acetanilide. The resulting compound was chlorinated with the equimolar amount of sulfuryl chloride in chloroform according to a conventional manner to form α-chloro-α-pivalyl-2,4-dichloro-5-(p-hexadecylbenzenesulfonamido)acetanilide, which was reacted with potassium salt of succinic acid imide in acetonitrile to give the exemplified coupler (1).

SYNTHESIS EXAMPLE 2

(Preparation of exemplified coupler 5)

α-Pivalyl-2-chloro-3,5-diaminoacetanilide was reacted with twofold mol of p-dodecylbenzenesulfonyl chloride to give α-pivalyl-2-chloro-3,5-di-(p-dodecylbenzenesulfonamido)acetanilide. The resulting compound was chlorinated according to a conventional manner to form α-chloro-α-pivalyl-2-chloro-3,5-di-(p-dodecylbenzenesulfonamido)-acetanilide, which was reacted in acetonitrile with equimolar amount of potassium salt of 2(1H) pyridone to give the exemplified coupler (5).

SYNTHESIS EXAMPLE 3

(Preparation of exemplified coupler 9)

α-Pivalyl-5-amino-2-chloroacetanilide was reacted with equimolar amount of p-dodecylbenzenesulfonyl chloride to give α-pivalyl-2-chloro-5-(p-dodecylbenzenesulfonamido)acetanilide. The resulting compound was chlorinated according to a conventional manner to form α-chloro-α-pivalyl-2-chloro-5-(p-dodecylbenzenesulfonamido)acetanilide, which was further reacted with equimolar amount of potassium salt of 1-benzyl-2-phenylurazol in acetonitrile to give the exemplified coupler (9).

SYNTHESIS EXAMPLE 4

(Preparation of exemplified coupler 10)

The process of Synthesis Example 3 was repeated, with the proviso that in place of potassium salt of 1-benzyl-2-phenylurasol, potassium salt of 5,5-dimethyl-2,4-thiazolidinedione was reacted to give the Exemplified coupler (10).

SYNTHESIS EXAMPLE 5

(Preparation of exemplified coupler 11)

The process of Synthesis Example 3 was repeated, with the proviso that 1,2-dibenzylurasol potassium salt was reacted in place of 1-benzyl-2-phenylurasol potassium salt to give exemplified coupler (11).

Elementary analysis data for the exemplified couplers according to the present invention, which were prepared by means of the aforementioned synthesis processes are shown below:

| Exemplified Coupler No. | | Elementary Analysis Value | | | | | |
|---|---|---|---|---|---|---|---|
| | | C | H | N | S | Cl | F |
| 1 | Calc'd | 61.24 | 7.24 | 5.49 | 4.19 | 9.27 | |
| | Found | 61.35 | 7.28 | 5.42 | 4.16 | 9.25 | |
| 2 | Calc'd | 62.38 | 7.17 | 6.23 | 4.75 | | 2.81 |
| | Found | 62.29 | 7.12 | 6.41 | 4.81 | | 2.65 |
| 3 | Calc'd | 65.74 | 6.98 | 9.38 | 3.58 | | |
| | Found | 65.67 | 6.95 | 9.42 | 3.60 | | |
| 4 | Calc'd | 58.70 | 6.87 | 7.20 | 8.24 | 4.56 | |
| | Found | 58.74 | 6.82 | 7.11 | 8.14 | 4.55 | |
| 5 | Calc'd | 65.26 | 7.80 | 5.63 | 6.45 | 3.56 | |
| | Found | 65.13 | 7.69 | 5.54 | 6.38 | 3.49 | |
| 6 | Calc'd | 58.11 | 7.37 | 8.68 | 7.95 | | |
| | Found | 58.26 | 7.48 | 8.59 | 7.86 | | |
| 7 | Calc'd | 65.90 | 6.82 | 8.17 | 3.74 | 4.13 | |
| | Found | 65.81 | 6.92 | 8.05 | 3.88 | 4.16 | |
| 8 | Calc'd | 68.76 | 7.65 | 7.71 | 3.53 | | |
| | Found | 68.65 | 7.75 | 7.77 | 3.50 | | |
| 9 | Calc'd | 65.57 | 6.70 | 8.31 | 3.80 | 4.20 | |
| | Found | 65.69 | 6.80 | 8.25 | 3.96 | 4.09 | |
| 10 | Calc'd | 60.01 | 6.99 | 5.83 | 8.90 | 4.92 | |
| | Found | 60.10 | 6.85 | 5.79 | 8.82 | 4.95 | |

-continued

| Exemplified Coupler No. | | Elementary Analysis Value | | | | | |
|---|---|---|---|---|---|---|---|
| | | C | H | N | S | Cl | F |
| 11 | Calc'd | 65.90 | 6.82 | 8.17 | 3.74 | 4.13 | |
| | Found | 65.99 | 6.97 | 8.26 | 3.90 | 4.18 | |
| 12 | Calc'd | 59.28 | 6.53 | 6.48 | 4.94 | 5.47 | |
| | Found | 69.15 | 6.49 | 6.50 | 4.92 | 5.52 | |
| 13 | Calc'd | 64.00 | 6.38 | 6.05 | 4.61 | 5.10 | |
| | Found | 64.11 | 6.42 | 6.21 | 4.51 | 5.03 | |
| 14 | Calc'd | 66.82 | 7.17 | 7.79 | 3.56 | 3.94 | |
| | Found | 66.85 | 7.29 | 7.61 | 3.52 | 3.91 | |
| 15 | Calc'd | 62.85 | 8.03 | 8.72 | 3.99 | 4.41 | |
| | Found | 62.90 | 8.04 | 8.90 | 3.81 | 4.41 | |
| 16 | Calc'd | 63.52 | 6.69 | 7.59 | 4.34 | 4.80 | |
| | Found | 63.80 | 6.72 | 7.65 | 4.24 | 4.75 | |
| 17 | Calc'd | 66.09 | 6.43 | 7.70 | 3.52 | 3.90 | |
| | Found | 66.03 | 6.42 | 7.90 | 3.65 | 3.91 | |
| 18 | Calc'd | 60.54 | 5.80 | 10.08 | 4.61 | 5.10 | |
| | Found | 60.52 | 5.83 | 9.96 | 4.69 | 5.03 | |
| 19 | Calc'd | 55.88 | 4.23 | 10.51 | 9.62 | 5.32 | |
| | Found | 55.72 | 4.11 | 10.41 | 9.60 | 5.31 | |
| 20 | Calc'd | 60.86 | 5.41 | 8.60 | 4.91 | | 5.44 |
| | Found | 60.62 | 5.28 | 8.72 | 5.03 | | 5.40 |
| 21 | Calc'd | 68.58 | 6.46 | 8.16 | 3.73 | | |
| | Found | 68.58 | 6.42 | 8.20 | 3.70 | | |
| 22 | Calc'd | 64.39 | 6.04 | 10.72 | 4.09 | 4.52 | |
| | Found | 64.42 | 6.06 | 10.65 | 4.15 | 4.52 | |
| 23 | Calc'd | 67.89 | 7.12 | 9.89 | 3.77 | | |
| | Found | 67.80 | 7.22 | 9.96 | 3.65 | | |
| 24 | Calc'd | 67.41 | 6.51 | 7.41 | 3.39 | | |
| | Found | 67.52 | 6.66 | 7.52 | 3.50 | | |
| 25 | Calc'd | 68.14 | 6.21 | 6.85 | 6.27 | | |
| | Found | 68.22 | 6.33 | 6.82 | 6.29 | | |
| 26 | Calc'd | 62.91 | 6.27 | 8.30 | 6.33 | 3.50 | |
| | Found | 63.09 | 6.31 | 8.42 | 6.42 | 3.62 | |
| 27 | Calc'd | 59.94 | 6.23 | 9.12 | 6.95 | 3.84 | |
| | Found | 59.87 | 6.32 | 9.24 | 7.08 | 3.91 | |
| 28 | Calc'd | 66.53 | 6.35 | 7.60 | 3.48 | 3.85 | |
| | Found | 66.44 | 6.14 | 7.62 | 3.59 | 3.87 | |
| 29 | Calc'd | 67.10 | 6.58 | 7.38 | 3.38 | 3.73 | |
| | Found | 67.33 | 6.49 | 7.35 | 3.30 | 3.77 | |
| 30 | Calc'd | 63.74 | 6.48 | 9.49 | 3.62 | 4.00 | |
| | Found | 63.85 | 6.44 | 9.61 | 3.50 | 4.04 | |
| 31 | Calc'd | 61.31 | 6.52 | 6.36 | 3.94 | 4.02 | |
| | Found | 61.41 | 6.49 | 6.45 | 3.99 | 3.96 | |
| 32 | Calc'd | 56.81 | 5.13 | 8.49 | 7.77 | 4.30 | |
| | Found | 56.89 | 5.20 | 8.36 | 7.72 | 4.26 | |
| 33 | Calc'd | 60.33 | 6.35 | 8.98 | 6.85 | 3.78 | |
| | Found | 60.26 | 6.33 | 8.89 | 6.76 | 3.75 | |
| 34 | Calc'd | 59.13 | 6.48 | 7.95 | 6.07 | 6.71 | |
| | Found | 59.22 | 6.54 | 7.86 | 6.02 | 6.69 | |
| 35 | Calc'd | 62.59 | 6.16 | 8.42 | 6.42 | 3.55 | |
| | Found | 62.55 | 6.24 | 8.39 | 6.48 | 3.49 | |
| 36 | Calc'd | 63.91 | 6.32 | 8.94 | 3.41 | 3.77 | |
| | Found | 63.96 | 6.35 | 8.86 | 3.35 | 3.79 | |
| 37 | Calc'd | 63.52 | 5.66 | 9.26 | 3.53 | 3.90 | |
| | Found | 63.56 | 5.72 | 9.09 | 3.48 | 3.84 | |
| 38 | Calc'd | 63.35 | 6.57 | 8.15 | 3.73 | 4.13 | |
| | Found | 64.32 | 6.52 | 8.10 | 3.66 | 4.20 | |

The yellow couplers according to this invention thus obtained show, as mentioned hereinbefore, satisfactory coupling reactivity even in the system of a color developing solution where no benzyl alcohol is added, and are substantially insusceptible against pH variation (pH 10.0–11.5). Further, the resulting dye image possesses good characteristics also with regard to preservability (light-stability, resistance against moisture and heat resistance).

For the formation of a yellow dye image by using the yellow coupler according to this invention, either of the so-called internal type process where said yellow coupler is included in a light-sensitive silver halide photographic material or the so-called external type process where said yellow coupler is included in a color developing solution can be used. For example, when the yellow coupler is applied according to the internal type process, inclusion of said yellow coupler into a silver halide emulsion may be effected, for example, by dissolving the coupler in a high-boiling organic solvent having the boiling point of higher than 175° C. such as dibutyl phthalate, dioctyl phthalate, triphenyl phosphate, tricresyl phosphate, phenoxy ethanol, diethyleneglycol monophenyl ether, diethoxyethyl phthalate, diethyllauryl amide and dibutyllauryl amide, or in a low-boiling organic solvent such as ethyl acetate, butyl acetate, methanol, ethanol, butanol, acetone, β-ethoxy ethyl acetate, methoxy triglycol acetate, dioxane and fluorinated alcohol, alone or mixed solvents. Thereafter, the solution is mixed with an aqueous gelatin solution containing a surface active agent. Then, the reaction solution is subjected to emulsification and dispersion by means of high speed rotation mixer or colloid mill and thereafter the resulting emulsion is directly added to silver halide emulsion, or after setting of the above emulsified and dispersed solution, extruding into noodle form is made and the low-boiling organic solvent is removed by means of washing with coater or the like. Thereafter, the residue may be added to the silver halide emulsion. Alternatively, such material as soluble in an alkali can be added according to the so-called Fischer dispersion method. The amount of yellow coupler to be added is preferably, in general, 10–300 g per mol of a silver halide and the amount may of course be variable due to the type of yellow coupler, objects for which the coupler is applied, etc.

To the light-sensitive silver halide color photographic material wherein the yellow coupler according to this invention is included, there can be added at the same time further couplers to form other dye images, such as cyan coupler, magenta coupler, etc. as well as various known additives for photograph.

As the cyan couplers which can preferably be used at the same time, a phenol or naphthol derivative is included, and as the colored cyan couplers, thre may be included a compound in which the coupling position of a colorless cyan coupler is substituted with an arylazo group or such colored cyan coupler as having the properties that the dye thereof reacts with the oxidation derivative of a color developing agent and elutes into the processing bath.

Further, as the magenta coupler which can preferably be used simultaneously, pyrazolone-, pyrazolotriazole-, pyrazolobenzimidazole- and indazolone-series compounds as well as colored magenta coupler are included and, more concretely, there may be included a compound in which the coupling position of a colorless magenta coupler is substituted by an arylazo group or such type of colored magenta coupler as having the properties that the dye thereof reacts with the oxidation derivative of a color developing agent and elutes into the processing liquid.

Furthermore, the light-sensitive silver halide color photographic material to which the yellow coupler according to this invention is applied, may include at the same time, if necessary, other yellow coupler, more concretely, a benzoylacetanilide- and pivaloylacetanilide-type yellow coupler as well as a 2-equivalent type yellow coupler in which the carbon atom at the coupling position is substituted with such substituent as being split off during the coupling reaction.

Further, with a view to improving sharpness and granularity of a dye image, it is possible to use a development inhibitor releasing type coupler (so-called DIR coupler) or a development inhibitor releasing type substance which does not form any dye by the reaction with the oxidation derivative of a developing agent. These materials may be used either alone or in combination of two or more of them.

The couplers and other substances mentioned hereinbefore can be added in order to satisfy the characteristic properties required for light-sensitive materials in such mode of addition that two or more of them are added to the same layer or the same compound is added to two or more different layers.

The light-sensitive silver halide photographic material to which the present invention is applied is constituted fundamentally from a support and a light-sensitive emulsion layer, further depending upon the type of light-sensitive silver halide color photographic materials, a sublayer, inter layer, filter layer, anti-curling layer, protective layer, etc. are superposed or applied in an appropriate combination thereof. Further, the light-sensitive layer itself may be constituted from, for example, a superposed layer which comprises layers showing higher speed or relatively lower speed in the same or different spectroscopic sensitivity region.

As the hydrophilic colloid which is conveniently used for the preparation of the light-sensitive emulsion, there are included modified gelatines such as alkali-treated gelatine, acid-treated gelatine, phenylcarbamylated gelatine, acylated gelatine, phthalated gelatine, etc. colloidal albumin, agar, gum arabic, cellulose derivatives such as hydrolysed cellulose acetate, carboxymethylcellulose, hydroxyethylcellulose, methylcellulose, etc., acrylamide, imidation product of polyacrylamide, casein, vinylalcohol polymer containing urethane carboxylic acid residue or cyanoacetyl group such as, for example, vinyl alcohol-vinyl cyanoacetate copolymer, polyvinyl alcohol, polyvinyl pyrrolidone, hydrolysed polyvinyl acetate, polymer obtainable by the polymerization between a protein or saturated acylated protein and a monomer containing vinyl group and the like.

As the silver halide used in the light-sensitive emulsion, there is included any one used ordinarily in the silver halide photographic emulsion such as silver bromide, silver chloride, silver iodobromide, silver chlorobromide, silver chloroiodobromide or the like.

These silver halides may be any type forming a latent image principally either on surface or inside of particles.

The silver halide emulsion to be used for the light-sensitive silver halide photographic material can be prepared by not only a process ordinarily employed but also various processes, for example, so-called process for the preparation of conversion emulsion which comprises forming an emulsion of silver salt particles having a higher solubility than silver bromide and comprising at least a part of silver salt and subsequently converting at least a part of the particle into silver bromide salt or silver iodobromide salt, or a process for the preparation of Lippmann emulsion which comprises a silver halide in the form of fine particles having less than $0.1\mu$ of average particle diameter.

The above-mentioned silver halide emulsion can be sensitized with a chemical sensitizer. Chemical sensitizers are roughly classified into 4 types of a noble metal sensitizer (such as chloroauric acid, potassium chloroaurate, etc.), sulfur sensitizer (such as active gelatine, sodium thiosulfate, etc.), selenium sensitizer (such as active and inert selenium compound, etc.) and reductive sensitizer (such as stannous salt, polyamine, etc.).

When a gold compound is used, ammonium thiocyanate or sodium thiocyanate can be used together.

Further, the photographic emulsion can be sensitized, if necessary, with respect to the strength in the spectral sensitization by the application of cyanine dyes such as cyanin, merocyanine, carbocyanine, etc. alone or in combination thereof, or by the application of such cyanine dye in combination with a styryl dye or the like.

Further, with a view to increasing stability of the formed dye image, there can be included p-substituted phenols in the emulsion layer and/or layer adjacent thereto of the light-sensitive silver halide photographic material to which the present invention is applied. Examples of particularly preferable p-substituted phenols are an alkyl-substituted hydroquinone, bishydroquinone, polymer series hydroquinone, p-alkoxyphenol, phenolic compound, etc. Also, an alkoxy or amyloxy derivative of 6-chromanol or 6,6'-dihydroxy-2,2'-spirochroman may be used in a similar manner.

The light-sensitive silver halide photographic material according to this invention is prepared by the application of said material on a support which has good planeness and less variation in the size during the preparation steps or processing steps. As such supports, films of cellulose acetate, cellulose nitrate, polyvinyl acetal, polypropylene, polyethylene terephthalate, polyamide, polycarbonate, polystyrene, etc., polyethylene laminate paper, polypropylene synthetic paper, baryta paper or the like can be used and these supports are appropriately selected according to the objects for use of light-sensitive silver halide photographic materials, respectively.

To those supports, there may be applied various subbing processes known heretofore in order to enhance adhesion between the silver halide emulsion layer.

Furthermore, the light-sensitive silver halide photographic materials to which the present invention is applied include every type of light-sensitive silver halide photographic materials such as color negative film, color positive film, color reversal film, color paper, etc.

In the method of forming dye image according to this invention, color development is conveniently effected, after imagewise exposure, according to a method of color development which is applied to an ordinary, so-called incorporated type light-sensitive silver halide color photographic material, but if necessary, so-called external type color treatment method may be applied. Alternatively, there can be supplied so-called diffusion transfer method which comprises contacting a lightsensitive layer and an image-receiving sheet in the developing liquid to form thereby a transferred image on the image-receiving sheet.

When the external type color processing method is applied in the present invention, there may be used, for example, a color developing liquid of the following composition:

2-Amino-5-diethylaminotoluene hydrochloride: 20 g
Anhyrous sodium sulfite: 20 g
Anhydrous sodium carbonate: 20 g
Potassium bromide: 1.0 g
Yellow coupler: 2.0 g
Water to make up: 1 liter As the yellow couplers of this invention which are suitable for use in the external type color processing method, the exemplified couplers (18), (19) and (20) may be included.

When the internal type color treatment method is applied in the present invention, such color developing liquid as having the composition of the above-mentioned external type color developing liquid excepting coupler is used as the color developing liquid for the internal type color treatment method. To such color developing liquid, pH adjustment is applied in conformity with objects for which it is used and further a variety of other photographic additives are added.

The color developing agents used in the present invention are aromatic primary amine compounds and particularly preferably those of p-phenylenediamine series, for example, 4-amino-N,N-dethylaniline, 3-methyl-4-amino-N,N-diethylaniline, 4-amino-4-ethyl-N-p-hydroxyethylaniline, 3-methyl-4-amino-N-ethyl-N-β-hydroxyethylaniline, 3-methyl-4-amino-N-ethyl-N-β-methanesulfonamido-ethylaniline, 3-methyl-4-amino-N-ethyl-N-β-methoxyethylaniline, 3-β-methanesulfonamido-ethyl-4-amino-N,N-diethylaniline, 3-methoxy-4-amino-N-ethyl-N-β-hydroxyethylaniline, 3-methoxy-4-amino-N-ethyl-N-β-methoxyethylaniline, 3-acetamido-4-amino-N,N-diethylaniline, 4-amino-N,N-dimethylaniline, N-ethyl-N-β-[β-(β-mthoxyethoxy)ethoxy]ethyl-3-methyl-4-aminoaniline, N-ethyl-N-β-(β-methoxyethoxy)ethyl-3-methyl-4-aminoaniline and salts thereof, for example, sulfate, hydrochloride, sulfite, p-toluenesulfonate, etc.

As the photographic additives to be added to such color developing liquids, there are mentioned an alkali agent (for example, a hydroxide, carbonate or phosphate of alkali metal or ammonium), pH adjusting agent or buffer (for example, a weak acid such as acetic acid or boric acid or weak base and salt thereof), development accelerator (for example, a pyridinium compound, cationic compound, potassium nitrate or sodium) nitrate, polyethyleneglycol condensation product or a derivative thereof, nonionic compound such as polythioether, polymer compound containing sulfite ester and other pyridines, ethanolamines, organic amines, benzyl alcohol, hydrazines, etc.), anti-fogging agent (for example, alkali metal bromide, alkali metal iodide, nitrobenzimidazoles as well as mercaptobenzimidazole, 5-methylbenzotriazole, 1-phenyl-5-mercaptotetrazole), compounds for use in rapid processing liquid, nitrobenzoic acid benzothiazolium derivative, phenazine N-oxides, stain or sludge inhibitor, superpose effect accelerator and preservative (for example, a sulfite, acid sulfite, hydroxylamine hydrochloride, formsulfite, alkanolamine sulfite addition product).

To the light-sensitive silver halide photographic material thus processed with such color developing liquid, there may be applied, after the development, each process selected from ordinary photographic processings, for example, those with such processing liquids as a stopping liquid containing an organic acid, a stopping and fixing liquid containing an organic acid and a fixing component such as hypo or ammonium thiosulfate, a fixing liquid containing the fixing component such as hypo or ammonium thiosulfate, a bleaching liquid comprising as the principal component ferric salt of aminopolycarboxylic acid and halogenated alkali, a bleaching and fixing liquid containing ferric salt of aminopolycarboxylic acid and the fixing component such as hypo or ammonium thiosulfate and other stabilizing liquid and washing with water and drying, in an appropriate combination thereof.

This invention will be illustrated by the following Examples.

EXAMPLE 1

Each of the exemplified couplers (1), (9), (11) and (17) was added in 20.0 g to a mixed liquid comprising 20 ml of dibutyl phthalate and 60 ml of ethyl acetate and warmed to 60° C. to give a complete solution. The resulting solution was mixed with 10 ml of a 10% aqueous solution of Alkanol B (alkylnaphthalenesulfonate; manufactured by Du Pont) and 200 ml of a 6% aqueous gelatin solution and then subjected to emulsification and dispersion in a colloid mill. The dispersion of the above coupler was added to 1 kg of a high speed silver iodobromide emulsion, coated on a film support and then dried to give a light-sensitive photographic material having stable coated film. The light-sensitive material thus obtained was, after being subjected to exposure in an ordinary manner, developed with a developing liquid having the composition as given below at 20° C. for 10 minutes, and subsequently subjected to each of the stopping, fixing and bleaching treatments in an ordinary manner.

Composition of Developing Liquid

N-Ethyl-N-β-methanesulfonamidethyl-3-methyl-4-aminoaniline hydrochloride: 5.0 g
Anhydrous sodium sulfite: 2.0 g
Benzyl alcohol: 3.8 g
Sodium carbonate (monohydrate): 50.0 g
Potassium bromide: 1.0 g
Sodium hydroxide: 0.55 g
Water to make up: 1 liter With regard to each of the samples thus obtained, maximum absorption wavelength (λmax), maximum density (Dmax) of the yellow image and preservability of the yellow image were measured. Futhermore, the same measurements as above were carried out with regard to comparative samples which were obtained by applying the same procedures as above-mentioned to a 4-equivalent type coupler of active point-unsubstituted type having the same mother structure as the exemplified coupler (1) [comparative coupler (1)], a 4-equivalent coupler of active point-unsubstituted type having the same mother structure as the exemplified couplers (9) and (11) [(comparative coupler (2)]and a 4-equivalent coupler of active point-unsubstituted type having the same mother structure as the exemplified coupler (17) [(comparative coupler (3)] as well as comparative couplers (4) and (5) as shown below. The results obtained are shown in table 1.

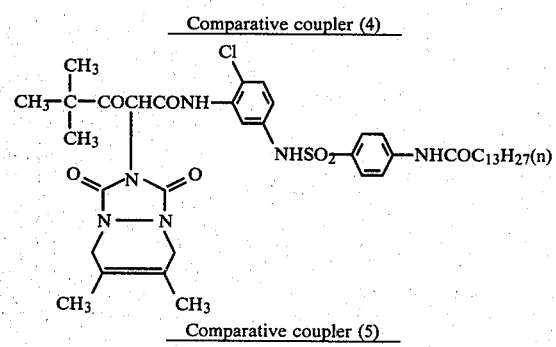

-continued

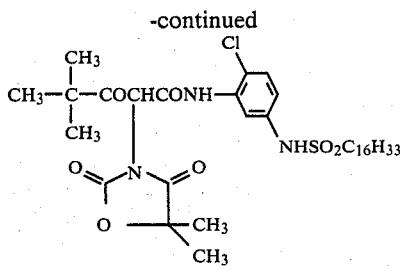

TABLE 1

| Coupler | $\lambda_{max}$ | $D_{max}$ | Yellow image Residue rate (%) Light stability | Moisture resistance |
|---|---|---|---|---|
| Comparative coupler (1) | 452 | 1.48 | 52 | 96 |
| Exemplified coupler (1) | 452 | 2.05 | 67 | 98 |
| Comparative coupler (2) | 450 | 1.59 | 60 | 97 |
| Exemplified coupler (9) | 450 | 2.47 | 69 | 97 |
| Exemplified coupler (11) | 450 | 2.45 | 72 | 98 |
| Comparative coupler (3) | 450 | 1.40 | 55 | 96 |
| Exemplified coupler (17) | 450 | 2.37 | 66 | 97 |
| Comparative coupler (4) | 450 | 2.26 | 57 | 95 |
| Comparative coupler (5) | 450 | 2.20 | 49 | 93 |

$\lambda_{max}$: Maximum spectral absorption wavelength (mµ)
$D_{max}$: Maximum density
Dye residue rate:
Dye residue in percent after the treatment of the portion having 1.0 of the initial density under the conditions given below.

Treatment conditions

Light stability: Irradiation with xenon arc lamp at 50° C. for 100 hrs.
Moisture resistance: Allowed to stand for 7 days at 50° C. and 80% of relative humidity.

As apparent from table 1, it is noted that the yellow couplers according to this invention possess good characteristics and are particularly useful as yellow couplers.

EXAMPLE 2

The exemplified coupler (8) was dispersed i a gelatin silver iodobromide single layer emulsion according to a similar procedure as that of Example 1. The amount of the silver halide used in this instance was half of that of Example 1.

As a comparative coupler, a 4-equivalent coupler of active point-unsubstituted type having the same mother structure as the exemplified coupler (8) [comparative coupler (6)] was used and the comparative sample was prepared in a similar manner as above except that the amount of silver used was two-fold of that used for the exemplified coupler (8).

Resulting samples after being subjected to exposure were developed by using the developing liquid shown in Example 1. With regard to each of the samples thus obtained, the concentration of the yellow dye to blue light in each of the steps was measured by means of a densitometer.

Results obtained are shown in the FIG. In the FIG., the abscissa represents the amount of exposure (log-E) and the ordinate represents concentration (D).

Further, in the FIG., the curve 1 is concerned with the use of the exemplified coupler (8) and the curve 2 is concerned with the use of the comparative coupler (6).

As apparent from the FIG., it is noted that a use of the yellow coupler according to this invention yields such images as having less fog, high photographic speed and good contrast.

EXAMPLE 3

20.0 g of each of exemplified couplers (1), (9) and (17), comparative coupler (5) as defined in Example 1 and a comparative coupler (7) having the structure as given below was added in 20.0 g to a mixed liquid of 20 ml of dibutyl phthalate and 60 ml of ethyl acetate amd warmed to 60° C. to form a complete solution. The resulting solution was mixed with 10 ml of a 6% aqueous solution of Alkanol B (alkylnaphthalenesulfonate; manufactured by Du Pont) and 200 ml of a 6% aqueous gelatin solution and then subjected to emulsification and dispersion in a colloid mill. The dispersion of each of the above couplers was added to 1 kg of silver chlorobromide (containing 80 mol% of silver bromide) emulsion, and applied on a polyethylene laminated paper and then dried to give a light-sensitive photographic material having stable coating film.

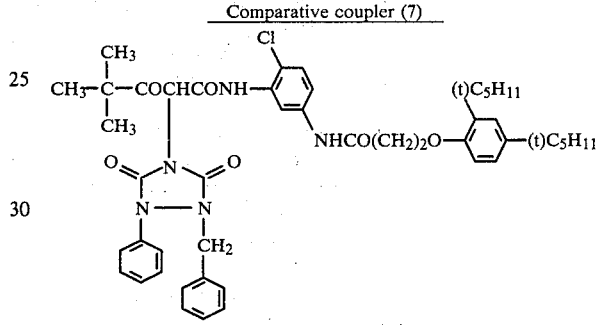

Comparative coupler (7)

To these samples was applied optical wedge exposure and thereafter various treatments were carried out at 30° C. according to the procedure as shown below, adjusting pH value of the color developing liquid with sodium hydroxide as defined in table 2 to give a colored image.

Processing procedure

Color development (3 min. and 30 sec.) →bleaching and fixing (1 min. and 30 min.) →washing with water (2 min.) →stabilization (1 min.) →drying. As the processing liquid, one having the following composition was used.

Composition of color developing liquid:
  Sodium hexametaphosphate: 2.5 g
  Anhydrous sodium sulfite: 1.9 g
  Sodium bromide: 1.4 g
  Potassium bromide: 0.5 g.
  Borax ($Na_2B_4O_7.10H_2O$): 39.1 g
  N-Ethyl-N-$\beta$-methanesulfonamidoethyl-4-aminoaniline hydrochloride: 5.0 g
  Water to make up: 1 liter
Composition of bleaching and fixing liquid:
  Ethylenediaminetetraacetic acid iron ammonium salt: 61.0 g
  Ethylenediaminetetraacetic acid diammonium salt: 5.0 g
  Ammonium thiosulfate: 124.5 g
  Sodium metabisulfite: 13.3 g
  Anhydrous sodium sulfite: 2.7 g
  Water to make up: 1 liter
  pH is adjusted to pH 6.5 with aqueous ammonia.
Composition of stabilizing liquid:

Glacial acetic acid: 20 ml

To this glacial acetic acid is added 800 ml of water and pH is adjusted to 3.5–4.0 with the addition of sodium acetate and then water is further added to make up 1 liter.

The maximum density of each of the resulting samples was compared and results thus obtained are shown in Table 2.

TABLE 2

|  |  | pH 10.0 | 10.5 | 11.0 | 11.5 |
|---|---|---|---|---|---|
| Exemplified coupler | (1) | 2.00 | 2.02 | 2.00 | 1.98 |
| " | (9) | 2.40 | 2.48 | 2.46 | 2.40 |
| " | (17) | 2.32 | 2.40 | 2.40 | 2.37 |
| Comparative coupler | (7) | 1.93 | 2.15 | 2.23 | 2.30 |
| " | (5) | 2.00 | 2.22 | 2.25 | 2.20 |

As shown in the above table 2, it appears that samples in which the exemplified couplers (1), (9) and (17) are used cause substantially no variation in color density over the pH range of pH 10–11.5 of a developer, whereas the comparative couplers (5) and (7) show outstanding variation. Thus, it is noted that the coupler according to the present invention is excellent.

EXAMPLE 4

After exposure of a light-sensitive material having an ordinary silver iodobromide emulsion layer, conventional external type color developing treatment was effected with an external color developing liquid as shown below, wherein each of exemplified couplers (18) and (20) and a coupler which has in the mother structure α-pivalyl-2-chloro-5-benzamidacetanilide and the same active point substitution component as that of the exemplified coupler (18) [comparative coupler (8)] was included. With regard to each of the resulting samples, fog, $\nu_{max}$ and Dmax were measured. Results obtained are shown below.

Composition of developing liquid:
  2-Amino-5-diethylaminotoluene hydrochloride: 2.0 g
  Anhydrous sodium sulfite: 2.0 g
  Anydrous sodium carbonate: 20.0 g
  Potassium bromide: 1.0 g
  Coupler: 2.0 g
  Water to make up: 1 liter

TABLE 3

| Coupler | Fog | λmax | Dmax |
|---|---|---|---|
| Comparative coupler (8) | 0.07 | 447 | 2.10 |
| Exemplified coupler (18) | 0.07 | 447 | 2.25 |
| Exemplified coupler (20) | 0.08 | 447 | 2.29 |

According to the above table 3, it is apparent that even when the yellow coupler of the present invention is used according to the external type of color developing treatment, excellent effect can also be achieved.

EXAMPLE 5

Exemplified couplers (12), (14) and (16) were dispersed in a gelatin-silver iodobromide single layer emulsion according to a similar procedures as those in Example 1. The amount of silver of the silver halide emulsion used in this instance was same as in Example 1. Further, comparative samples were prepared by a similar process as that employed for the preparation of the exemplified couplers, using comparative couplers (10), (11) and (12) which contain α-pivalyl-2-chloro-5-(2,4-ditert.-amylphenoxybutanamido)acetanilide in the mother structure and such active point substitution components as the same as those of exemplified couplers (12), (14) and (16), respectively, and a comparative coupler (13) which contains in the mother structure α-pivalyl-2-chloro-5-hexadecanesulfonamide and in which the active point substitution component is the same as that of the exemplified coupler (16). After the application of white exposure to each of the above samples through optical wedge, the color development was carried out according to high temperature rapid processing step as defined below.

| Treatment Steps (38° C.) | Processing time |
|---|---|
| Color development | 3 min. 15 sec. |
| Bleaching | 6 min. 30 sec. |
| Washing with water | 3 min. 15 sec. |
| Fixing | 6 min. 30 sec. |
| Washing with water | 3 min. 15 sec. |
| Stabilization | 1 min. 30 sec. |

Composition of the treating liquid used in each of the above treatment steps is as follows:

Composition of color developer:
  4-Amino-3-methyl-N-ethyl-N-(β-hydroxyethyl)-aniline sulfate: 4.8 g
  Anhydrous sodium sulfite: 0.14 g
  Hydroxylamine ½ sulfate: 1.98 g
  Sulfuric acid: 0.74 g
  Anhydrous potassium carbonate: 28.85 g
  Anhydrous potassium hydrogen carbonate: 3.46 g
  Anhydrous potassium sulfite: 5.10 g
  Potassium bromide: 1.16 g
  Sodium chloride: 0.14 g
  Nitrilotriacetic acid 3 sodium salt (monohydrate): 1.20 g
  Potassium hydroxide: 1.48 g
  Water to make up: 1 liter Composition of beaching liquid:
  Ethylenediaminetetraacetic acid iron ammonium salt: 100.0 g
  Ethylenediaminetetraacetic acid diammonium salt: 10.0 g
  Ammonium bromide: 150.0 g
  Glacial acetic acid: 10.0 ml
  Water to make up: 1 liter
  pH being adjusted to 6.0 with aqueous ammonia.

Composition of fixing liquid:
  Ammonium thiosulfate: 175.0 g
  Anhydrous sodium sulfite: 8.6 g
  Sodium metasulfite: 2.3 g
  Water to make up: 1 liter
  pH being adjusted to 6.0 with acetic acid.

Composition of stabilizing liquid:
  Formalin (37% aqueous solution): 1.5 ml
  Konidax (manufactured by Konishiroku Photo Industry Co., Ltd.): 7.5 ml
  Water to make up: 1 liter With regard to each of samples thus obtained results are given in table 4.

TABLE 4

| | Yellow image | | | |
|---|---|---|---|---|
| | | | Residue rate (%) | |
| Coupler | λmax | Dmax | Light stability | Moisture resistance |
| Comparative coupler (10) | 446 | 1.85 | 70 | 97 |
| Exemplified coupler (12) | 450 | 2.30 | 68 | 98 |
| Comparative coupler (11) | 446 | 2.07 | 72 | 97 |
| Exemplified coupler (14) | 450 | 2.42 | 69 | 98 |

TABLE 4-continued

| | | | Yellow image | |
|---|---|---|---|---|
| | | | Residue rate (%) | |
| Coupler | λmax | Dmax | Light stability | Moisture resistance |
| Comparative coupler (12) | 446 | 1.76 | 75 | 98 |
| Exemplified coupler (16) | 450 | 2.14 | 70 | 98 |
| Comparative coupler (13) | 450 | 1.96 | 64 | 97 |

As apparent from the above table 4, the couplers according to this invention are attainable good effects even when they are applied to high temperature and rapid processing.

Furthermore, even when the above samples of this invention were subjected to reversal development processing, similarly good yellow image was obtained.

EXAMPLE 6

On a support comprising subbed transparent cellulose triacetate base, each of the following layers was applied in the order of succession as mentioned beginning from the side of said support to form light-sensitive high speed multi-layer color negative material, multi-layer sample-1.

Layer 1

Antihalation layer

A gelatin solution containing black colloid silver was coated at the rate of 0.3 g of silver/m². (dry film thickness 3µ)

Layer 2

Inter Layer

An aqueous gelatin solution was coated. (dry film thickness 1µ)

Layer 3

Red sensitive low speed silver halide emulsion layer

After being chemically sensitized with gold sensitizer and sulfur sensitizer, a silver iodobromide emulsion containing 4 mol% of silver iodide (average grain diameter 0.4µ) was further spectral sensitized by the addition per mol of the silver halide of 0.25 g of D-(1) and 0.06 g of D-(2) which have the structures as defined below, respectively, as a red sensitive sensitizing dye, and then 1 g of 4-hydroxy-6-methyl-1,3,3a,7-tetrazaindene and 40 mg of 1-phenyl-5-mercaptotetrazol were added and furthermore cyan coupler dispersion material-1 was added thereto. The red sensitive low speed silver halide emulsion thus obtained was coated at the rate of 18 g of silver/m². (dry film thickness 3.8µ)

Layer 4

Red sensitive high speed silver halide emulsion layer

After being chemically sensitized with gold sensitizer and sulfur sensitizer, a silver iodobromide emulsion containing 7 mol% of silver iodide (average grain diameter 1.2µ) was further color sensitized by the addition per mol of the silver halide of 0.13 g of D-(1) and 0.3 g of D-(2) as red sensitive sensitizing dyes, and then 1 g of 4-hydroxy-6-methyl-1,3,3a,7-tetrazaindene and 12 mg of 1-phenyl-5-mercaptotetrazol were added and furthermore cyan coupler dispersion material-2 was added thereto. The red sensitive, high speed silver halide emulsion thus obtained was at the rate of 10 g of silver/m². (dry film thickness 2µ)

Layer 5

Inter layer

This is the same as the layer 2.

Layer 6

Green sensitive, low speed silver halide emulsion layer

After being chemically sensitized with gold sensitizer and sulfur sensitizer, a silver iodobromide emulsion containing 5 mol% of silver iodide (average grain diameter 1.2µ) was further spectral sensitized by the addition per mol of the silver halide of 0.11 g of D-(3), 0.08 g of D-(4) and 0.09 g of D-(5) which have the structures as defined below, respectively, as green sensitive sensitizing dye, and then 1 g of 4-hydroxy-6-methyl-1,3,3a,7-tetrazaindene and 40 mg of 1-phenyl-5-mercaptotetrazol were added and furthermore magenta coupler dispersion material-1 was added thereto. The green sensitive, low speed silver halide emulsion thus obtained was coated at the rate of 14 g of silver/m². (dry film thickness 4µ)

Layer 7

Green sensitive, high speed silver halide emulsion layer

After being chemically sensitized with gold sensitizer and sulfur sensitizer, a silver iodobromide emulsion containing 7 mol% of silver iodide (average grain diameter 1.2µ) was further spectral sensitized by the addition per mol of the silver halide of 0.09 g of D-(3), 0.07 g of D-(4) and 0.08 g of D-(5) as green sensitive sensitizing dyes, and then 1 g of 4-hydroxy-6-methyl-1,3,3a,7-tetrazaindene and 10 mg of 1-phenyl-5-mercaptotetrazol were added and furthermore magenta coupler dispersion material-2 was added thereto. The green sensitive, low speed silver halide emulsion thus obtained was coated at the rate of 12 g of silver/m². (dry film thickness 1.8µ)

Layer 8

Inter layer

This is the same as the layer 2.

Layer 9

Yellow filter layer

An aqueous gelatin solution containing yellow colloidal silver and 2,5-di-tert.-octylhydroquinone dispersion material was coated at the rate of 0.1 g of silver/m².

Layer 10

Blue sensitive, low speed silver halide emulsion layer

After chemically sensitizing a silver iodobromide emulsion containing 8 mol% silver iodide (average grain diameter 0.6µ) with gold sensitizer and sulfur sensitizer, 1 g of 4-hydroxy-6-methyl-1,3,3a,7-tetrazaindene, 80 mg of 1-phenyl-5-mercaptotetrazol and 2 g of 1,2-bisvinylsulfonylethane were added furthermore yellow coupler dispersion material was added thereto. The blue sensitive, low speed silver halide emulsion thus obtained was coated at the rate of 5 g of silver/m².

Layer 11

Blue sensitive, high speed silver halide emulsion layer

After chemically sensitizing a silver iodobromide emulsion containing 7 mol% of silver iodide (average grain diameter 1.2μ) with gold sensitizer and sulfur sensitizer, 60 mg of 4-hydroxy-6-methyl-1,3,3a,7-tetrazaindene and 2 g of 1,2-bisvinylsulfonethane were added and furthermore yellow coupler dispersion material was added thereto. The blue sensitive, high speed silver halide emulsion thus obtained was coated at the rate of 7 g of silver/m². (dry film thickness 3μ)

Layer 12

Protective layer

An aqueous gelatin solution containing 1,2-bisvinylsulfonethane was coated (dry film thickness 1.2μ)

The sensitizing dyes used have the following structures:

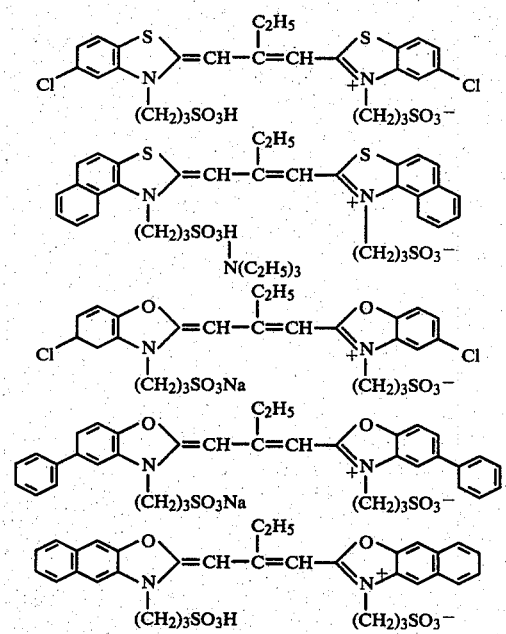

Coupler dispersion materials used for the above layers 3, 4, 6, 7, 10 and 11, respectively were prepared as follows:

Cyan coupler dispersion material-1

39 g of 1-hydroxy-N-[δ-(2,4-di-tert.-amylphenoxy)-butyl]-2-naphthamide as the cyan coupler, 2 g of 1-hydroxy-4-[4-(1-hydroxy-8-acetamido-3,6-disulfo-2-naphthylazo)phenoxy]-N-[δ-(2,4-di-tert.-amylphenoxy)butyl]-2-naphthamido-disodium salt as the colored coupler and 2.5 g of 2-(1-phenyl-5-tetrazolthio)-4-octadecylsuccinimido-1-indanone as the DIR compound were dissolved in a mixture of 22 g of tricresylphosphate and 140 g of ethyl acetate and added to 450 ml of 7.5% gelatin solution containing 1.5 g of Alkanol B. The resulting solution was emulsified and dispersed in a colloid mill.

Cyan coupler dispersion material-2

Each of the couplers used in the above dispersion solution-1 was used in the amount of 45 g of cyan coupler, 2 g of colored coupler and 2.5 g of DIR compound. These couplers were dissolved together with 0.5 g of lauryl gallate in a mixture of 25 g of tricresyl phosphate and 150 g of ethyl acetate and added to 480 ml of 7.5% gelatin solution which contains 1.7 g of Alkanol B. The resulting solution was emulsified and dispersed in a colloid mill.

Magenta coupler dispersion material-1

50 g of 1-(2,4,6-trichlorophenyl)-3-[3-(2,4-di-tert.-amylphenoxyacetamido)benzamido]-5-pyrazolone as the magenta coupler, 10 g of 1-(2,4,6-trichlorophenyl)-4-(1-naphthylazo)-3-(2-chloro-5-octadecylsuccinimidanilino)-5-pyrazolone as the colored coupler and 1.5 g of 2-(1-phenyl-5-tetrazolylthio)-4-octadecylsuccinimido-1-indanone as the DIR compound were dissolved in a mixture of 60 g tricresyl phosphate and 180 g of ethyl acetate and was added to 670 ml of 7.5% gelatin solution which contains 2 g of Alkanol B. The resulting solution was emulsified and dispersed in a colloid mill.

Magenta coupler dispersion material-2

10 g of 1-(2,4,6-trichlorophenyl)-3-[3-(2,4-di-tert.-amylphenoxyacetamido)benzamido]-5-pyrazolone as the magenta coupler, 2.9 g of 1-(2,4,6-trichlorophenyl)-4-(4-methoxyphenylazo-3-[3-(2,4-di-tert.-amylphenoxyacetamido)benzamido]-5-pyrazolone as the colored coupler and 1 g of 2,4-di-tert.-octylhydroquinone were dissolved in a mixture of 20 g of tricresylphosphate and 45 g of ethyl acetate and added to 170 ml of 7.5% gelatin solution which contains 2 g of Alkanol B. The resulting solution was emulsified and dispersed in a colloid mill.

Yellow coupler dispersion material 200 g of the exemplified compound (9) as the yellow coupler were dissolved in a mixture of 100 g of dibutylphosphate and 560 g of ethyl acetate and added to 1500 ml of 75% gelatin solution which contains 22 g of Alkanol B. The resulting solution was emulsified and dispersed in a colloid mill.

Further, as a comparative sample, a multi-layer sample-2 was prepared quite in the same manner as the sample-1 except that the yellow coupler in the layer 10 and layer 11 of the sample-1 was replaced with α-pivalyl-α-[4-carboxyphenoxy)-2-chloro-5-(n-dodecanesulfonamido)acetanilide.

The resulting sample was exposed in a similar manner as in Example 5 and subjected to color development treatment. Results thus obtained are shown in table 5.

TABLE 5

| | Sensitivity | Fog | $D_{max}$ | Light stability | Moisture resistance |
|---|---|---|---|---|---|
| Sample - 1 | 127 | 0.13 | 2.48 | 77 | 98 |
| Sample - 2 | 100 | 0.12 | 2.30 | 77 | 55 |

As apparent from the above table 5, it is noted that the sample-1 wherein the coupler according to this invention is used is particularly superior to the sample-2 in the sensitivity and wet resistance.

EXAMPLE 7

A dispersion liquid was prepared from the exemplified coupler (14) in a similar manner as in Example 1. The dispersion liquid thus prepared was added to 1 kg of a gelatin-silver chlorobromide emulsion (chloride 80%, bromide 20%) and applied on a polyethylene-laminated paper and then dried to give a light-sensitive material. After application of light wedge exposure to this light-sensitive material, development was effected for 3.5 minutes in a color developing bath having the following composition:
Benzyl alcohol: 50 ml
Sodium hexametaphosphate: 2.50 g
Anhydrous sodium sulfite: 1.85 g
Sodium bromide: 1.40 g
Potassium bromide: 0.50 g
Borax: 39.1 g
N-Ethyl-$\beta$-methanesulfonamidoethyl-3-methyl-4-aminoaniline sulfate: 5.0 g
Water to make up: 1 liter Subsequently, the light-sensitive material was immersed in the bleaching and fixing bath having the following composition for 2 minutes:
Ethylenediaminetetraacetic acid iron ammonium salt: 61.0 g
Ammonium thiosulfate: 124.5 g
Sodium metabisulfite: 13.3 g
Anhydrous sodium sulfite: 2.7 g
Ethylenediaminetetraacetic acid diammonium salt: 5.0 g
Water to make up: 1 liter After washing with running water for 2 minutes, the light-sensitive material was immersed in the following stabilizing bath for 1 minute:
Glacial acetic acid: 25 ml
Pure water: 800 ml
Water to make up (after adjustment of pH to 3.5–4.0 with sodium acetate trihydrate): 1 liter Then, after subjecting to spray rinse with running water for 10–15 seconds, the light-sensitive material is dried to give yellow image excellent in the transparency.

4. Brief Explanation of Drawings:

The drawing illustrates Example 2 of this invention. Abscissa represents amount of exposure (log-E) and ordinate represents concentration (D), the curve 1 is one obtained by using the exemplified coupler (8) and the curve 2 is one obtained by using the comparative coupler (6).

What we claim is:

1. A method of forming a dye image, comprising: processing a light-sensitive silver halide photographic material after its imagewise exposure in the presence of a compound of the following general formula (I) and an aromatic primary amine color developing agent:

General Formula (I)

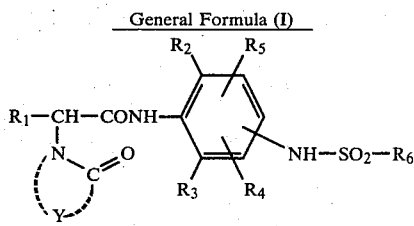

wherein $R_1$ represents cyano, alkyl carbonyl, phenylalkyl carbonyl, phenoxy alkyl carbonyl, phenylthio alkyl carbonyl, arylcarbonyl, alkyl phenyl carbonyl, alkoxy phenyl carbonyl, $R_2$, $R_3$, $R_4$, and $R_5$ independently are hydrogen, halogen, alkyl, alkoxy, aryloxy, alkylacyloxy, arylacyloxy, acylamino, N-alkyl carbamoyl, N-phenylcarbamoyl, alkylsulfonamido, arylsulfonamido, N-alkyl sulfamoyl, N-phenylsulfamoyl, or imido, $R_6$ represents cycloalkyl, alkenyl, naphthyl, thienyl, benzothienyl, furyl, or pyranyl, or a group of the formula (II):

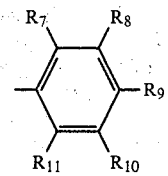

wherein $R_7$, $R_9$ and $R_{11}$ are each hydrogen or alkyl, the sum of the carbon atoms in $R_7$, $R_9$ and $R_{11}$ being 5 to 20, $R_8$ and $R_{10}$ are hydrogen, and Y represents non-metal atoms required for forming 2,5-dioxo-imidazolidine, 2-3,5-trioxo-imidazolidine, 2,5-dioxo-triazolidine, 2,4-oxazolidinedione, 2,4-thiazolidinedione, 2(1H)-pyridone, 2(1H)-pyrazone, 5(1H)-imidazolone, 5(1H)-triazolone, 2(1H)-pyrimidone, 2-pyrazolone (5), 2-isothiazolone(5), 2(1H)-quinaoxazolone, 4(3H)-pyrimidone, 2-benzoxazolone, 4-isooxazolone(5), 3-fluorone(2), 4-imidazolone(2), 3-pyrazolone, 2-tetrazolone(5), 3-tetrazolone(5), and derivatives thereof.

2. A method according to claim 1, wherein $R_2$ and $R_3$ in the compound of the general formula (I) are individually a hydrogen or halogen atom, or an alkoxy or aryloxy group.

3. A method according to claim 2, wherein at least one of $R_2$ and $R_3$ is a halogen atom.

4. A method according to claim 1, wherein the compound is represented by the following general formula (III):

General Formula (III):

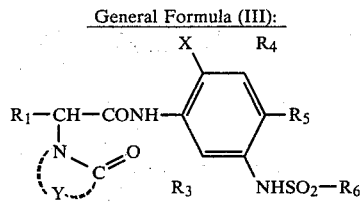

wherein $R_1$ represents cyano, alkyl carbonyl, phenylalkyl carbonyl, phenoxy alkyl carbonyl, phenylthio alkyl carbonyl, arylcarbonyl, alkyl phenyl carbonyl, alkoxy phenyl carbonyl, $R_3$, $R_4$ and $R_5$ represent independently hydrogen, halogen, alkyl, alkoxy, aryloxy, alkylacyloxy, arylacyloxy, acylamino, N-alkyl carbamoyl, N-phenyl carbamoyl, alkylsulfonamido, arylsulfonamido, N-alkyl sulfamoyl, N-phenyl sulfamoyl, or imido, $R_6$ represents cycloalkyl, alkenyl, naphthyl, thienyl, benzothienyl, furyl, or pyranyl, or a group of the formula (II):

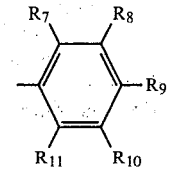

wherein $R_7$, $R_9$ and $R_{11}$ are each hydrogen or alkyl, the sum of the carbon atoms in $R_7$, $R_9$ and $R_{11}$ being 5 to 20, $R_8$ and $R_{10}$ are hydrogen, and Y represents non-metal atoms required for forming 2,5-dioxo-imidazolidine, 2-3,5-trioxoimidazolidine, 2,5-dioxo-triazolidine, 2,4-oxazolidinedione, 2-4-thiazolidinedione, 2(1H)-pyridone, 2(1H)-pyrazone, 5(1H)-imidazolone, 5(1H)-triazolone, 2(1H)-pyrimidone, 2-pyrazolone(5), 2-isothiazolone(5), 2(1H)-quinaoxazolone, 4-(3H)-pyrimidone, 2-benzoxazolone, 4-isooxazolone(5), 3-fluorone(2), 4-imidazolone(2), 3-pyrazolone, 2-tetrazolone(5), 3-tetrazolone(5), and derivatives thereof.

5. A method according to claim 4, wherein $R_1$ represents a pivalyl group.

6. A method according to claim 5, wherein $R_6$ represents a group represented by following Formula (II):

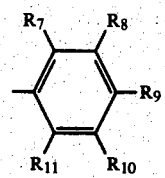

wherein $R_7$, $R_9$ and $R_{11}$ are each hydrogen or alkyl, the sum of the carbon atoms in $R_7$, $R_9$ and $R_{11}$ being 5 to 20, $R_8$ and $R_{10}$ are hydrogen and Y represents non-metal atoms required for forming 2,5-dioxo-imidazolidine, 2-3,5-trioxoimidazolidine, 2,5-dioxo-triazolidine, 2,4-oxazolidinedione, 2,4-thiazolidinedione, 2(1H)-pyridone, 2(1H)-pyrazone, 5(1H)-imidazolone, 5(1H)-triazolone, 2(1H)-pyrimidone, 2-pyrazolone(5), 2-isothiazolone(5), 2(1H)-quinaoxazolone, 4(3H)-pyrimidone, 2-benzoxazolone, 4-isooxazolone(5), 3-fluorone(2), 4-imidazolone(2), 3-pyrazolone, 2-tetrazolone(5), 3-tetrazolone(5), and derivatives thereof.

7. The method according to claims 1, 4 or 6 wherein the alkyl and/or alkoxy of said alkyl phenyl carbonyl and said alkoxy phenyl carbonyl has 1 to 5 carbon atoms.

8. The method according to claims 1, 4 or 6 wherein said sum is 8 to 16.

9. The method according to claim 1 wherein $R_6$ is cycloalkyl, alkenyl, naphthyl, thienyl, or a group of the formula

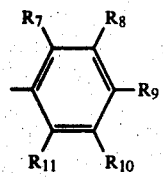

* * * * *